US012569571B2

(12) United States Patent　　　(10) Patent No.:　US 12,569,571 B2
Chandran　　　　　　　　　　　　(45) Date of Patent:　　Mar. 10, 2026

(54) SALT RESPONSIVE NANOGELS AND NANOPARTICLES

(71) Applicant: HOWARD UNIVERSITY, Washington, DC (US)

(72) Inventor: Preethi Chandran, Washington, DC (US)

(73) Assignee: Howard University, Washington, DC (US)

( * ) Notice: Subject to any disclaimer, the term of this patent is extended or adjusted under 35 U.S.C. 154(b) by 277 days.

(21) Appl. No.: 18/207,167

(22) Filed: Jun. 8, 2023

(65) Prior Publication Data

US 2023/0310646 A1　　Oct. 5, 2023

Related U.S. Application Data

(62) Division of application No. 16/310,608, filed as application No. PCT/US2017/039034 on Jun. 23, 2017, now Pat. No. 11,707,534.

(60) Provisional application No. 62/354,372, filed on Jun. 24, 2016.

(51) Int. Cl.
| | |
|---|---|
| *A61K 47/69* | (2017.01) |
| *A61K 9/00* | (2006.01) |
| *A61K 48/00* | (2006.01) |
| *C08G 73/02* | (2006.01) |
| *C08J 3/075* | (2006.01) |
| *C08J 3/12* | (2006.01) |
| *C08J 3/24* | (2006.01) |
| *C08L 79/02* | (2006.01) |
| *B82Y 5/00* | (2011.01) |
| *C08K 5/00* | (2006.01) |
| *C08K 5/07* | (2006.01) |
| *C08L 101/14* | (2006.01) |

(52) U.S. Cl.
CPC ........ *A61K 47/6935* (2017.08); *A61K 9/0004* (2013.01); *A61K 9/0053* (2013.01); *A61K 48/0041* (2013.01); *C08G 73/0206* (2013.01); *C08J 3/075* (2013.01); *C08J 3/12* (2013.01); *C08J 3/24* (2013.01); *C08J 3/246* (2013.01); *C08L 79/02* (2013.01); *A61K 48/0033* (2013.01); *B82Y 5/00* (2013.01); *C08G 2210/00* (2013.01); *C08J 2300/14* (2013.01); *C08J 2379/02* (2013.01); *C08K 5/0025* (2013.01); *C08K 5/07* (2013.01); *C08L 101/14* (2013.01)

(58) Field of Classification Search
CPC ........................... A61F 47/6935; C08G 73/02
See application file for complete search history.

(56) References Cited

U.S. PATENT DOCUMENTS

| | | | |
|---|---|---|---|
| 6,333,051 | B1 | 12/2001 | Kabanov et al. |
| 2014/0135376 | A1 | 5/2014 | Engbersen et al. |

OTHER PUBLICATIONS

Motorov , Stimulus Responsive Hollow Capsules by Material and Efficient and Robust Cross-Linking Precipitation Revisited, Langmuir, vol. 27, Issue 24, pp. 15305-15311. (Year: 2011).*

(Continued)

*Primary Examiner* — Carlos A Azpuru
(74) *Attorney, Agent, or Firm* — Sughrue Mion, PLLC

(57) ABSTRACT

Covalently linked linear polyethylenimine (PEI) clusters are provided that change conformation depending upon changes in counterion concentrations. The structures may be used for the storage, delivery, and/or transport of substances.

11 Claims, 14 Drawing Sheets

(56) References Cited

OTHER PUBLICATIONS

Glutaraldehyde, Handbook of Biopolymers and Biodegradable Plastics. (Year: 2013).*

Bahulekar, Raman, et al., "Polyethyleneimine in Immobilization of Biocatalysts," Enzyme Microb. Technol., 1991, 13: 858-868.

Kato, Kazuaki, et al., "Cooperativity and Selectivity in Chemomechanical Polyethylenimine Gels," Langmuir, 2007, 23(21): 10741-10745.

Kokufuta, Etsuo, "Polyelectrolyte Gel Transitions: Experimental Aspects of Charge Inhomogeneity in the Swelling and Segmental Attractions in the Shrinking," Langmuir, 2005, 21(22): 10004-10015.

Lupitskyy, Robert, et al., "Robust Synthesis of Nanogel Particles By An Aggregation-Crosslinking Method." Soft Matter, 2010, 6: 4396-4402.

Motornov, Mikhail, et al., "Stimuli-Responsive Hydrogel Hollow Capsules by Material Efficient and Robust Cross-Linking Precipitation Synthesis Revisited," Langmuir, 2011, vol. 27: Issue 24 15305-15311.

* cited by examiner

A

B

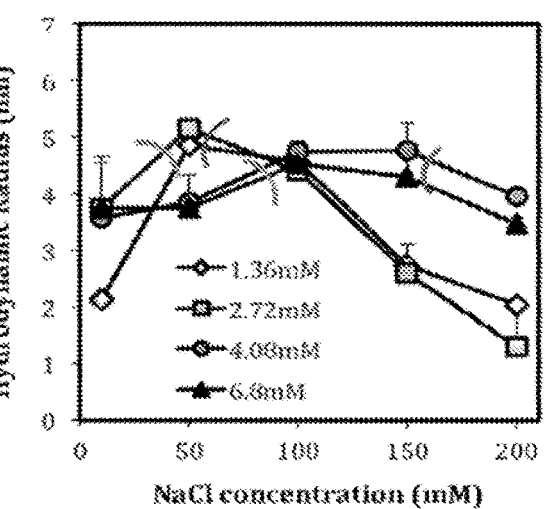
FIG. 7a
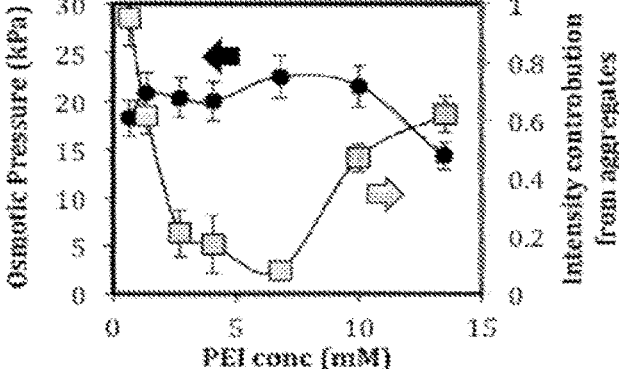
FIG. 7b
FIG. 7c

SALT RESPONSIVE NANOGELS AND NANOPARTICLES

CROSS-REFERENCE

This is a divisional of application Ser. No. 16/310,608, filed Dec. 17, 2018, which is a 371 of PCT/US2017/039034, filed Jun. 23, 2017, which claims benefit of 62/354,372, filed Jun. 24, 2016.

FIELD

The present disclosure relates generally to chemical storage and/or delivery vehicles that selectively release or expose molecules or other nanoscale substances to a target environment with salt changes.

BACKGROUND

There are numerous variations of delivery vehicles for the transport of various substances. For instance, a wide array of excipients for pharmaceutical dosage forms have been developed, including for oral and intravenous dosage forms. However, many problems exist with respect to delivering the transported substance to a target site intact. For instance, active molecules of oral pharmaceutical compositions are often partially metabolized or degraded early in the digestive tract, reducing their effectiveness by diminishing the concentration of active molecules prior to arrival in the colon or other areas where rapid uptake is accomplished. Chronic oral administration may include a host of side effects depending on the formulation of the oral dosage form, including for example the formation of gastric ulcers. Oral dosage forms may also take a fair amount of time to provide effective pain relief since the dosage form generally will need to dissolve and release the transported drug in certain areas of the gastrointestinal tract before a patient experiences the effects of the drug. While intravenous delivery may solve this problem to an extent, it is less convenient and less desirable to most patients.

Many dosage forms have been developed to target specific areas of the digestive tract. For instance, some oral dosage forms include one or more envelopes or coatings of substances that are degraded at specific points during the digestion process. For instance, a coating for a composition may include carbohydrate substances if release early in in the digestive process is desired, or may contain a higher concentration of lipids for delivery later in the digestive process. Nevertheless, existing modes of oral delivery often are either subject to early release due to partial degradation of the excipient or take a significant time for digestive mechanisms to effect release of active molecules once delivered to the target site.

Environment-responsive materials have been developed for use in the pharmaceutical industry and other applications. Such materials undergo changes in structure in response to changes in environmental variables such as temperature or pH. These changes in structure may be utilized to effect release of therapeutic molecules only in environments having specific characteristics, allowing targeted delivery of the therapeutic molecules. However, many environment-responsive materials respond only to relatively large changes in environmental conditions, making it difficult to effect changes within the body of a living animal, or keep the stability of the released or stored material.

SUMMARY

This disclosure relates generally to structures of covalently linked linear polyethyleniniine (PEI) clusters that change conformation, for instance between swollen and collapsed states, depending upon counterion concentrations for the storage and/or delivery and/or transport of substances. The PEI structures change their conformation and three-dimensional structure in response to changing salt or ion concentrations, and can be engineered to release or expose carried molecules at certain conditions while holding and/or protecting the carried molecules from exposure at other conditions.

In some forms, linear PEI is aggregated to form a nanostructure that captures and releases small substances dependent on changes in environmental conditions. In some forms, the nanostructure may be a nanocompartent that substantially surrounds an internal space in one configuration and exposes the internal space in another configuration. In some particular forms, the PEI structures comprise crosslinked, unbranched polyethyleniniine molecules that forms a relatively impermeable shell at high and low salt concentrations but becomes a semi-permeable gel at physiological salt concentrations within the small intenstine, so that the structure protects delivered molecules when in environments with certain salt levels but exposes the delivered molecules when in an environment having a specific range of salt concentration.

In some forms, linear (i.e. unbranched) PEI is crosslinked with an amine crosslinking agent that reacts with secondary amines, especially antifunctional crosslinker with end groups reacting with secondary amines. In some forms, linear PEI is crosslinked with an amine crosslinking agent including one or more aldehyde groups. In certain embodiments, the amine crosslinking agent is glutaraldehyde or another molecule with two or more aldehyde groups.

The crosslinked linear PEI forms a housing scaffold which may be associated with molecules, compounds, or nanoparticles, protecting them in one configuration but allowing the molecules, compounds, or nanoparticule to be released, exposed, sensed, captured, and/or absorbed in another configuration based on the concentration of negative ions surrounding the scaffold. In some forms, the linear PEI is from about 0.5 kDa to bout 50 kDa, preferably from about 2.5 kDA to about 25 kDA, prior to crosslinking. The polymer is responsive to relatively subtle changes in negative ion concentration, including from salts as common as sodium chloride. In some forms, the polymer becomes a swollen semi-permeable gel capable of absorbing or releasing small particles at chloride ion concentrations of about 100 to about 200 mM, but relatively minor shifts of chloride ion concentration to outside of that range (for example to a range of Cl* concentration less than 50 mM or a range of Q-concentration greater than 250 mM) can cause the polymer to enter a shrunken state in which it forms a relatively impermeable barrier around associated particles. These changes in salt concentration are relatively easily attainable in the human body, allowing the change in PEI conformation to take place readily within a human host. The relatively minor changes in salt concentration required for switching between three-dimensional structure also make the technology suitable and easy to sue in a wide variety of other applications, and are compatible with use of a wide variety of molecules and materials to be stored, transported, or delivered. Many molecules and materials are highly stable at the levels of salt used to trigger switching of forms.

Transported matter carried by the PEI scaffold may comprise a wide variety of matter, including but not limited to macromolecules of various types, active pharmacological substances, proteins, nucleic acids, carbohydrates, enzymes, nanosensors, and nanochips.

Alternatively, in some forms PEI aggregates may be provided in the form of nanobrushes wherein PEI is bound to a substrate. A nanobrush may be formed that comprises linear polyethyleneimine chains bound to a substrate by a crosslinking agent reactive with a primary amine group, with PEI extending from the substrate into the surrounding environment. The nanobrush is transitionable between a first state and a second state in response to surrounding anion concentrations, so that the PEI chains of the nanobrush may be induced to contract and ensnare or cling to matter or extend to release matter as desired.

The salt-responsive structures described herein may be used for selective storage of therapeutic or sensor/detection molecules or materials. In some forms, substrate or activating molecules diffusing in and out of the nanostructure or separated from the therapeutic or sensor/detection materials dependent upon changes in salt conditions. In other forms, selective release of a sensor, therapeutic, detection, activating, or substrate molecule from the nanostructure is effected by switching salt conditions.

BRIEF DESCRIPTION OF THE DRAWINGS

FIGS. 7a to 7c are graphs demonstrating hydrophobic polyelectrolyte dynamics of PEI.

DETAILED DESCRIPTION

Figure 1:
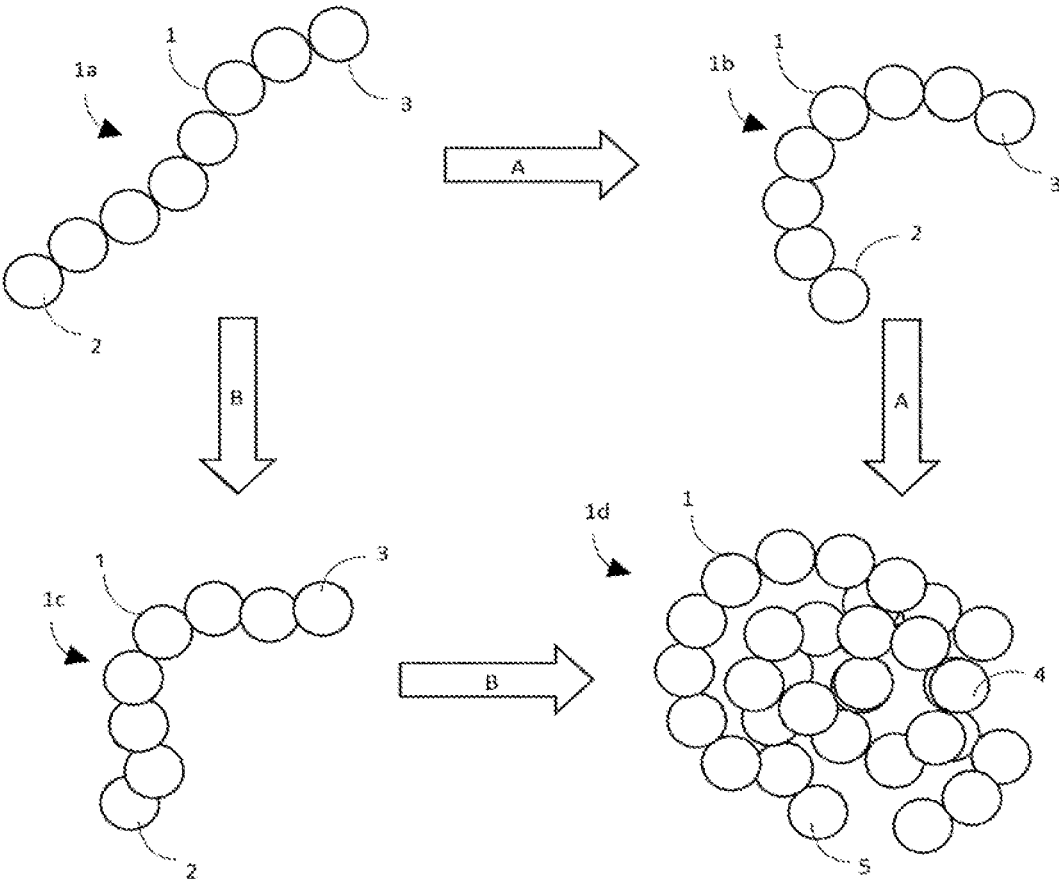
FIG. 1 shows the general conformation of an unbranched molecule of PEI under changing environmental conditions.

Linear (unbranched) PEI is a cationic polymer that has closely-spaced amines with weak-base protonation capacity, and a hydrophobic backbone that is kept unaggregated by intra-chain repulsion. As a result, in solution PEI exhibits multiple buffering mechanisms, and polyelectrolyte states that shift between aggregated and free forms. The polymer consists of amines separated by ethylene groups, as shown below in Formula I:

$$CH_2—(NH_2{}^+—CH_2—CH_2)_n—NH_2{}^+—CH_2—CH_3 \qquad (I)$$

Without wishing to be bound by theory, it is believed that in an acidic environment the PEI chain is positively charged due to protonation of the secondary amines along the backbone. Since the polymer can take up protons, it exhibits weak-base buffering properties, allowing it to protect other molecules from acidic environments. PEI also is a hydrophobic polymer because of its ethylene-rich backbone.

The conformation of the charged hydrophobic PEI polymer strongly depends on the solution conditions. The backbone extension of the hydrophobic polyelectrolyte depends on the competition between inter- and intra-chain interactions. Intra-chain charge repulsion (i.e., repulsion between the amine groups on the same chain) favors chain extension, whereas inter-chain repulsion (i.e. repulsion between groups on different chains) may compact the molecule. Charge interactions in polyelectrolyte solution are long-range, and inter-chain charge repulsion may occur at relatively low concentrations. When there is insufficient backbone charge to keep the molecule extended by intra-chain charge repulsion, the polymer collapses or aggregates. Solution conditions can affect the balance between inter- and intra-chain repulsion. For instance, pH increases the charge of the polymer, while added salt generally reduces charge repulsion due to screening of electrostatic interactions. Increasing PEI concentration generally increases interchain effects, promoting collapse or compaction of PEI molecules. At low-ionic strength the attractive hydrophobic interactions between the polymer segments are often counterbalanced by the electrostatic repulsion, so that an extended molecular conformation is observed.

Unlike in many polyelectrolytes, the charged groups of PEI are located directly on the backbone and separated by only two ethylene groups. Such close spacing of these charged groups results in the protonation of one amine group affecting the ability of neighboring amine groups to be protonated, increasing the charge-repulsion in its vicinity and therefore the free energy of protonation. In addition, the neighborhood charge repulsion will be sensitive to the extension or aggregation state of the polymer backbone, i.e. its hydrophobic polyelectrolyte properties. Studies have shown that that titration analysis of PEI requires accounting for two- and three-neighbor influence on amine protonation, and in fact requires 100× more free energy for 50% protonation of amines in the PEI backbone than in its non-polymeric counterpart, dimethyl-amine (the apparent pKa of PEI is about 7, whereas the pKa of dimethylamine is about 10).

PEI may be functionalized in a number of drug-delivery applications, with the degree of functionalization depending on PEI's protonated state and the extent of aggregation. In addition, PEI's charging properties determine its binding with molecules such as nucleotides and the stability of PEI complexes in the acidic environment of cell uptake vesicles.

Free and aggregate forms of PEI also have different biological toxicities, with free forms disrupting cells and cellular vesicles by inserting into their negative-charged lipid membranes and aggregate forms sequestering opposite-charged proteins and entities in the blood stream and rendering them ineffective for delivery. Strategies for reducing the toxicity of PEI need to account for its polyelectrolyte state in different solution conditions.

FIG. 1 illustrates the general changes in conformation that a molecule of PEI undergoes when subjected to different environmental conditions. In the presence of moderate salt concentrations (e.g. 100-200 mM), inter-chain repulsion between amine groups will cause the PEI polymer chain 1 to have a relatively extended conformation so that ends 2 and 3 of the chain are distant from one another. Increasing the concentration of PEI (Arrow "A") results in an increase in inter-chain interactions, causing the PEI chain 1 to collapse into a more compact structure 1a and bringing ends 2 and 3 closer. As PEI concentration further increases, the polymer chain 1 takes on an even more compact structure Id, and tends to aggregate with other polymer chains (such as chains 4 and 5). Similarly, increases in negative ion concentration (Arrow "B") cause the PEI chain 1 to take on a more compact form (1c) due to decreases in intra-chain repulsion among amine groups. Further increases in negative ion concentration cause the chain to take on the aggregated form Id. The pH of a solution mainly affects charge of PEI molecules, not aggregation, meaning that relatively minor changes in salt concentration can effectively transform the shape of PEI nanogels regardless of pH, although some minor adjustments to ranges may be necessary at very high or low pH.

When crosslinked, unbranched PEI forms a nanogel mass that shrinks or swells when subjected to these changing conditions. Crosslinking agents used to bind PEI may include crosslinking molecules having functional groups reactive with secondary amines. One preferred example of crosslinking agent for this purpose is glutaraldehyde. This allows the crosslinked PEI mass to be manipulated via changing ion concentrations in order to act as a vehicle for other molecules and small particles. In some forms, the transported molecules or compounds have a largest dimension of less than about 500 nm, or less than about 400 nm, or less than about 300 nm, or less than about 200 nm, or less than about 100 nm, or less than about 50 nm, or less than about 25 nm, or less than about 10 nm. In some forms, PEI nanocompartments comprise aggregates of unbranched PEI from about 2.5 kDa to about 25 kDa, and may have an overall length from about 50 nm to about 500 nm, preferably about 50 nm to about 200 nm. These nanocompartments are nanogels that transition between a porous or open state and a less porous closed state in response to anion concentrations, so that transitioning between the two states can be induced by the addition of compounds as simple as table salt or water.

Figure 2A:
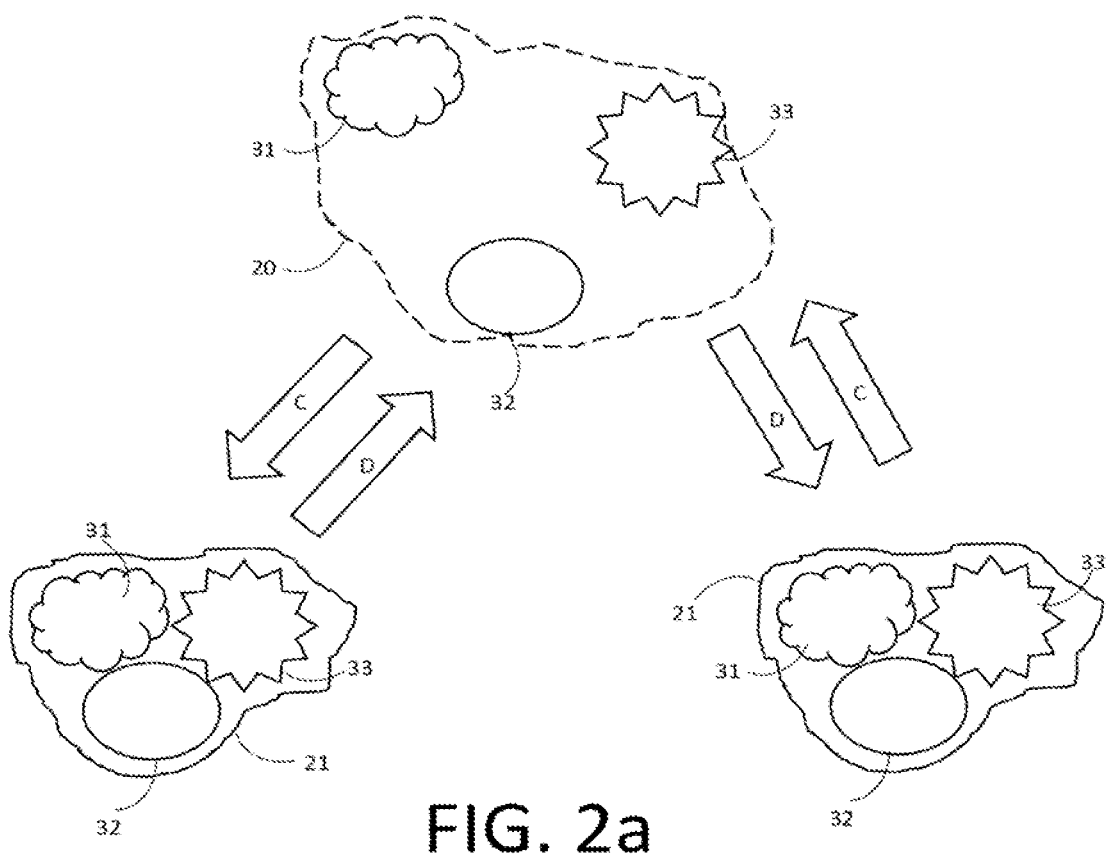
FIG. 2a illustrates the reversible compaction of PEI nanocompartments under changing salt concentrations.

As shown in FIG. 2a, at certain Cl⁻ concentrations (about 100-200 mM) crosslinked PEI forms a semi-permeable gel 20 that allows small molecules and particles to pass through it and interact with larger molecules of particles 31, 32, and 33 held within the gel nanostructure. However, increasing or decreasing the Cl⁻ concentration outside of this range causes the gel structure to collapse due to compaction of the PEI molecules as previously described, reducing the size of the crosslinked PEI aggregate and reducing permeability. Thus, as negative ionic concentration is reduced (for instance, by adding water to a solution containing the PEI gel 20), as shown by Arrow "C" of FIG. 2, the PEI compacts to form a relatively impermeable shell 21 or "shrink wrap" around particles 31, 32, and 33. In this shell 21 particles 31, 32, and 33 are held in a compact association, and remain well protected from the environment. This effect is reversible, so that adding sodium chloride or another anion source (Arrow "D") causes the PEI molecules to expand, resulting a return to the semi-permeable gel form having PEI molecules spaced further apart, making it easier for outside molecules to interact with stored particles 31, 32, and 33. In some cases, transitioning from compact shell form 21 to gel form 20 may also result in complete release of one or more of particles 31, 32, and 33. Further increasing anion concentration when in the gel form (Arrow "D") will also cause the semi-permeable gel 20 to enter a relatively impermeable shell form 21, which is reversible by diluting the anion concentration (e.g. by adding water) (Arrow "C"). Thus, the crosslinked PEI aggregates readily adopt compact shell forms when placed in simple and readily available solutions such as potable water or salt water, and become more permeable at intermediate anion concentrations (such as in the small intestine).

Figure 2B:
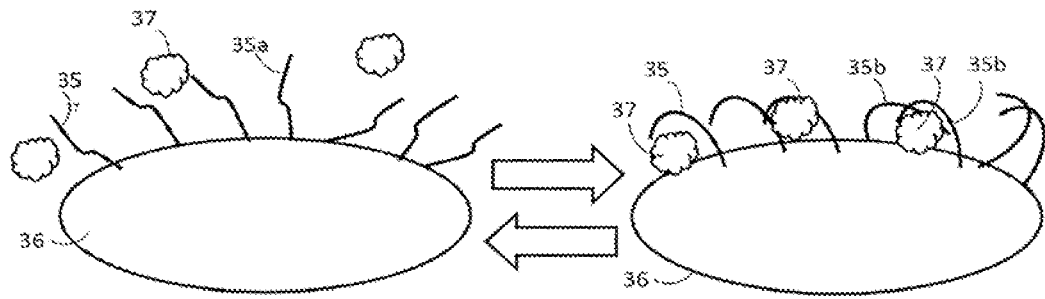
FIG. 2b illustrates the reversible capture and release of matter using a PEI nanobrush.

An alternative form of carrier is shown in FIG. 2b, wherein amine-terminated unbranched PEI chains 35 are anchored to a substrate 36 to form a nanobrush. The PEI polymer 35 is formed via a process resulting in a terminal amine group and as a result may be linked to the substrate 36 via a variety of crosslinking agents having functional groups reactive with secondary amines so that they are capable of bonding with the ends of PEI chains. The substrate 36 may be any surface capable of bonding with the crosslinking agent or molecules associated with the crosslinking agent.

As with the nanogel particles described above, the nanobrushes are reactive to environmental conditions and reversibly change conformation based on relatively minor changes in surrounding anion concentration. As shown in FIG. 2b, when PEI is in a relatively relaxed state, due to intra-chain repulsion, macromolecules 37 are relatively free to engage and disengage with the nanobrushes. By raising or lowering anion concentration, such as by concentrating or diluting salt concentration, the PEI chains 35 anchored to the substrate 36 adopt a more compact conformation 35b, entrapping macromolecules 37. In this manner, ion concentration may be manipulated in order to use PEI nanobrushes to scrup or ensnare macromolecules or small particles. For instance, the nanobrushes may be released in a liquid and combined with amounts of salt sufficient to ensnare suspended macromolecules or other particles and then removed by changing the salt and pH.

Figure 3:
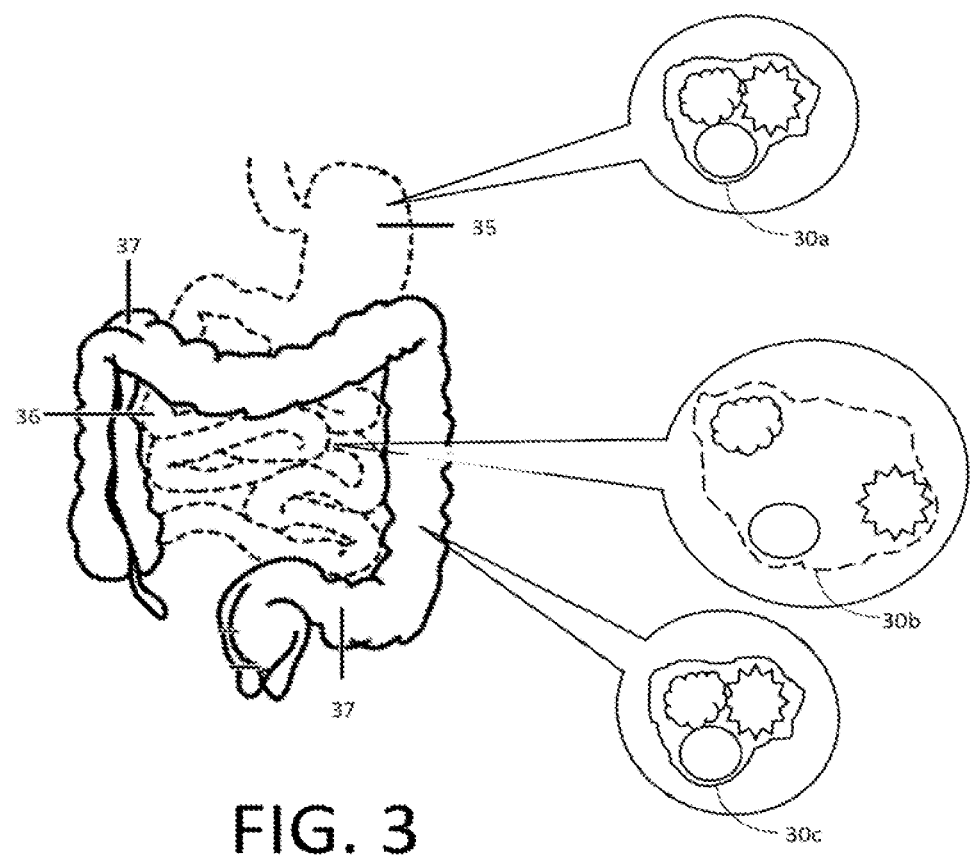
FIG. 3 shows the changing state of one form of PEI nanogel carrier during transit through a human digestive system.

Due to the range of chloride or other ion concentrations in which some forms of the crosslinked PEI gels become compact, which conveniently overlaps the physiological levels normally found in the small intestine, they may be used as vehicles for safely delivering therapeutic agents, sensors, and other particles safely past the harsh conditions of the stomach and into the small intestine, where swelling of the PEI structure automatically results in exposure or release of the transported particles. As shown in FIG. 3, a compact PEI carrier structure 30a ingested by a patient will remain in its compact state during early digestion due to the conditions within the environment of the stomach 35, where high salt content and acidic pH maintain the carrier structure in a collapsed form. As the carrier structure moves to the small intestine 36, it encounters lower salt concentrations and a neutral pH, causing the carrier to swell to an uncondensed semi-permeable gel. This allows particles contained within the carrier structure to interact with the surrounding environment, and in some cases results in full release of transported matter. The carrier again enters a compact form 30c in the large intestine 37 and is easily excreted.

The collapsed form of PEI carriers can protect transported matter and result in more efficient delivery of particles to the small intestine. Macromolecules such as proteins, vaccines, antigens, and hormones are desirable for a number of reasons. For instance, they can be produced on a commercial scale relatively easily, can perform complex functions with a specificity not attainable by small molecules, and often have reduced cytotoxicity due to greater specificity and biocompatibility. Some macromolecules may be used to replace malfunctioning proteins and damaged DNA product in vivo. As a result of the increased specificity and reduced safety concerns, many macromoleculescan be more quickly approved for use than small molecules by administrative agencies such as the U.S. Food and Drug Administration. Oral delivery of these macromolecules can be quite beneficial, because delivery does not require invasive techniques or specialized personnel. Oral dosage forms are also generally less expensive, generate less waste, and result in better patient compliance due to ease of use. Further, uptake of the macromolecules follows natural transport routes of the patient's body. However, often delivery of macromolecules via oral dosage forms is inefficient, resulting in less than about 1% bioavailability relative to the amount ingested. Passage of oral dosage forms through the stomach results in breakdown of many macromolecules due to the acidic pH of the environment and peptidases that cleave peptide bonds. Macromolecules that survive intact into the small intestine encounter a relatively neutral pH, but rapid secretion and turnover of viscous mucus on the epithelial surface hampers drug diffusion to the cell surface. As a result, only a small amount of a typical orally-administered macromolecule ever reaches the target site. These problems may be overcome by transporting the carrier within a PEI nanogel carrier, where the compact conformation automatically assumed by the carrier structure within the environment of the stomach protects the macromolecules from peptidases and acid hydrolysis, resulting in more effective delivery of intact macromolecules to the small intestine.

PEI carriers may be combined with one or more additional excipients. In some embodiments, the PEI carriers may be incorporated into edible compositions. Advantageously, compositions incorporating PEI carriers may in some forms have an ionic concentration that maintains the carriers in a compact state until dissociation of some or all of the composition during digestion releases the carriers into an environment that induces swelling of the carriers.

The PEI carriers are inexpensive and easily manufactured, and provide a broad spectrum delivery platform that does not need to be tailored for individual macromolecules. Rather than binding to a specific type of macromolecule, the PEI carriers discussed herein rely upon the collapse of the overall carrier structure to trap and hold macromolecules and other particles. Formulation of the carrier structures is easily scalable, as is incorporation of particles for transport. While there are some minor concerns with toxicity of PEI, the polymer is currently used in human patients and cytotoxicity concerns are further reduced by crosslinking PEI chains so that the carrier structure is excreted by the patient without significant release of free polymer.

Figure 4:
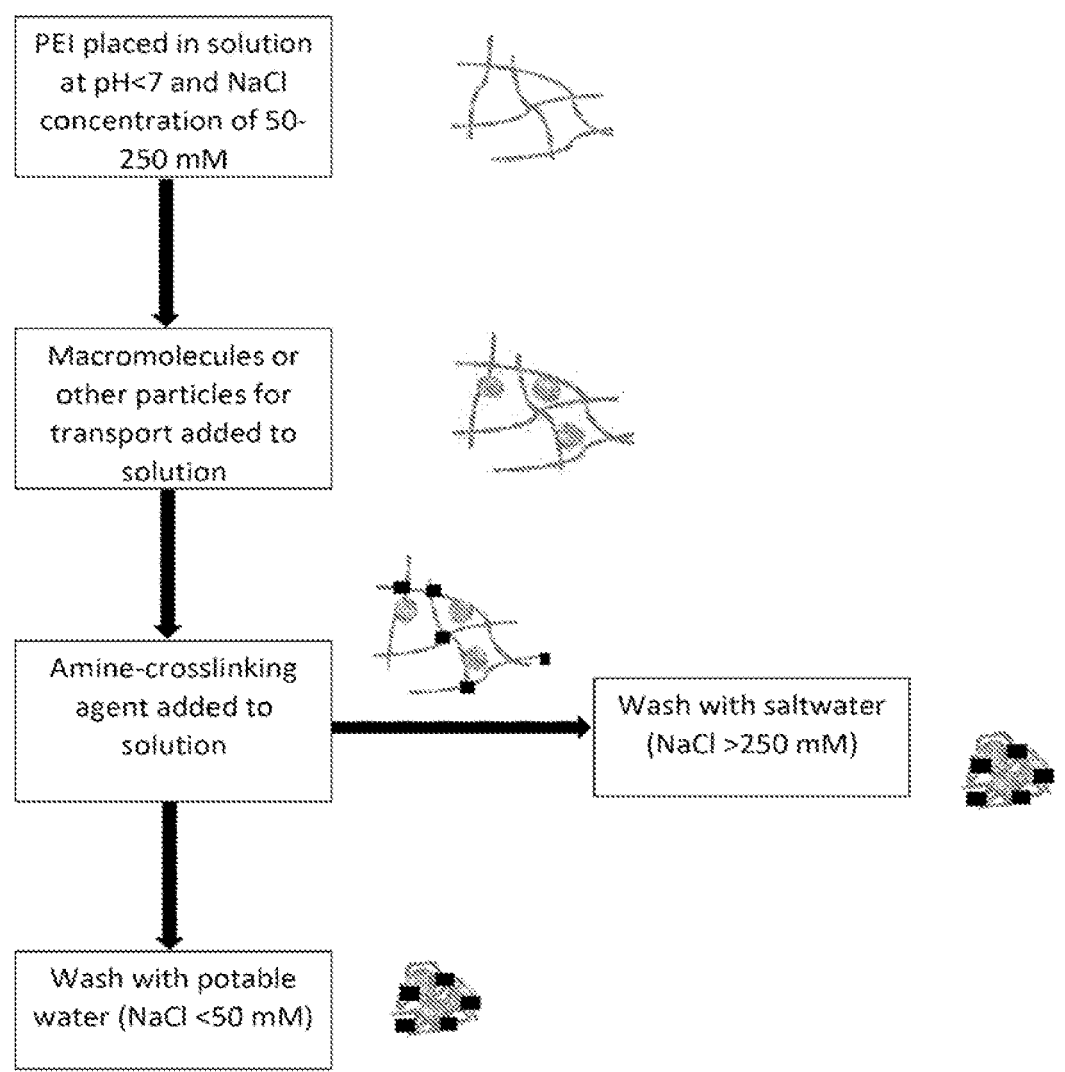
FIG. 4 illustrates the formation and manipulation of compactible PEI nanogels.

Preparation and use of PEI nanogel carrier is simple, and is illustrated in FIG. 4. PEI is added to a solution having a pH below about 7 and a concentration of sodium chloride between about 50 and 250 mM, preferably between about 100 to 200 mM, where the PEI chains are positively charged and remain outstretched in a free polymer state. Particles to be transported, preferably negatively-charged particles which will be drawn to the PEI, are added to the solution. A crosslinking agent, preferably an amine crosslinking agent, is added to the solution in order to crosslink the PEI and entrap particles to be transported. Suitable crosslinking agents include glutaraldehyde, formalin, and other bifunctional crosslinking agents with end groups reactive with secondary amine groups. While maintained in the solution, the crosslinked PEI loosely holds the particles to be transported, but the carrier structure has sufficient porosity for small molecules to diffuse into the structure. Washing with water having less than about 50 mM NaCl, preferably less than about 10 mM NaCl, collapses the PEI carrier structures without affecting the charge of the PEI chains themselves. Loaded PEI carriers may be concentrated by filtration or other known techniques prior to or after collapse of the carriers. The loaded PEI carriers may then be incorporated into various compositions having a NaCl concentration below about 50 mM, preferably below about 10 mM, and will automatically expand to a porous, permeable state when subjected to conditions wherein the NaCl concentration is about 50 mM to about 250 mM, preferably about 100 to about 200 mM. Whether in the collapsed or expanded state, crosslinking structures maintain the relative arrangement of PEI chains, preventing disassociation of the carrier structures and permitting the carriers to be expanded and compacted repeatedly.

Alternatively, after crosslinking of PEI to form loaded carrier structures, the loaded carriers may be washed with a solution high in salt (e.g. greater than about 250 mM) in order to induce compaction of the carrier structure. In this manner, the loaded carriers may be incorporated into compositions having a high salt concentration in order to release or expose transported matter when subjected to lower salt environments having a NaCl concentration between 50 mM and 250 mM.

Example 1

Formation of salt-responsive PEI aggregates was confirmed using multiple techniques. PEI (2.5 kDa, Polysciences Inc) was mixed with water (1 μm sterile-filtered and molecular biology grade, Sigma Aldrich, St. Louis, MO) to obtain a final PEI concentration of 13.6 mM in amine groups. The mixture was dissolved by heating to ~80° C. and adding HCl to reduce the pH to ~7.5. The 13.6 mM stock solution was sterile-filtered (Acrosidic 32 mm Syringe Filters with 0.2 pm Supor membrane, Pall Corporation, MD) for subsequent use.

Along with every PEI stock solution, a control polymer-free solution was prepared that was subjected to the same HO additions and heat treatments as the stock. Every subsequent dilution, salt addition, and pH modification that was performed on the PEI stock was also performed on aliquots of the polymer-free solution. These polymer-free solutions were used as the controls for the osmotic and light scattering experiments performed on the corresponding PEI solutions.

PEI solutions of different salt content and pH were prepared and equilibrated overnight. Salt-free DNA in water was added to the PEI solutions to achieve final concentration of 2 ng/μl DNA. Nanoparticles were formed as the DNA packed in the PEI. The solution was incubated at room temperature overnight and the nanoparticles' hydrodynamic radii were measured by Malvern Zetasizer ZS.

A 100 mM aqueous solution of ninhydrin reagent (Sigma Aldrich, New York) was added to 3 ml of PEI solution (concentration: 1-8 mM) to obtain a final ninhydrin concentration of 3 mM. The solution was vortexed vigorously for 1 minute, and kept in a hot water bath (70-80° C.) for 20-25 minutes. A yellow-orange color developed due to the reaction between ninhydrin and secondary amines. The solution tubes were then placed in a cold water bath (5° C.) for about 10 minutes and the absorbance at 487 nm was measured with a UV-Visible spectrophotometer (Cary 5000 LTV-Vis NIR spectrophotometer, Varian Inc, CA). The color was stable for about 24 hours.

Figure 5A:
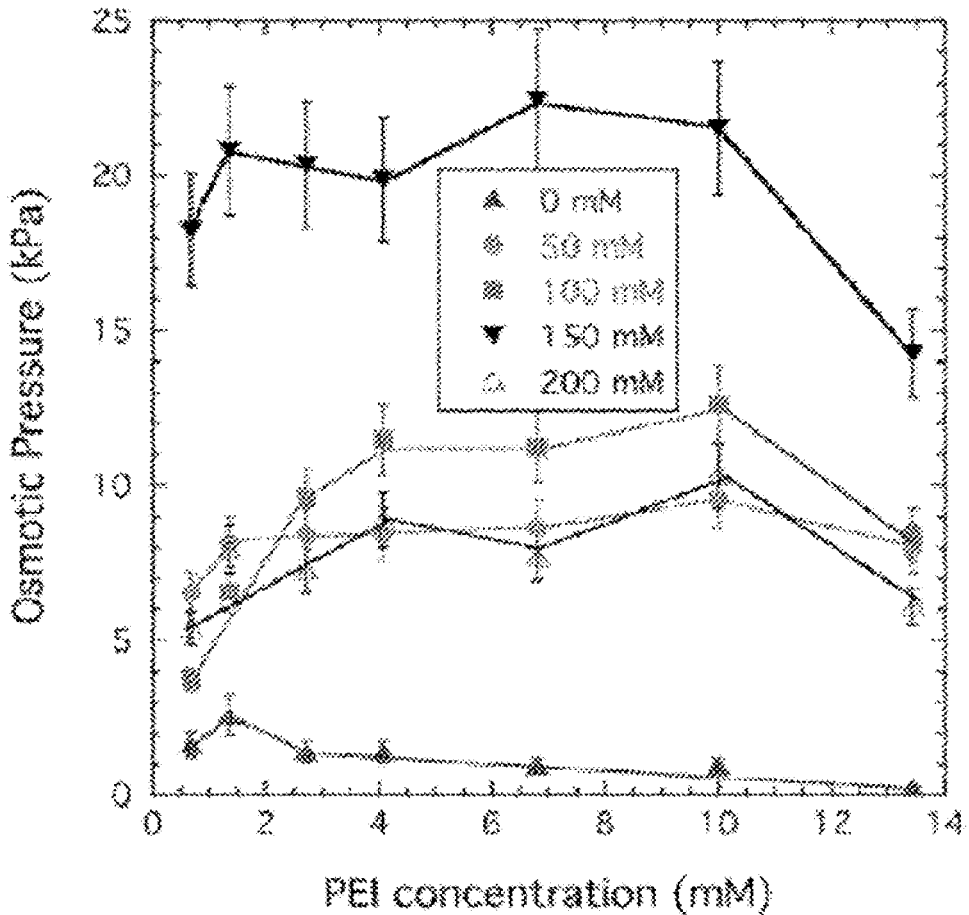
FIG. 5a is a graph that shows osmotic pressure of PEI solutions as a function of PEI concentration.
Figure 5B:
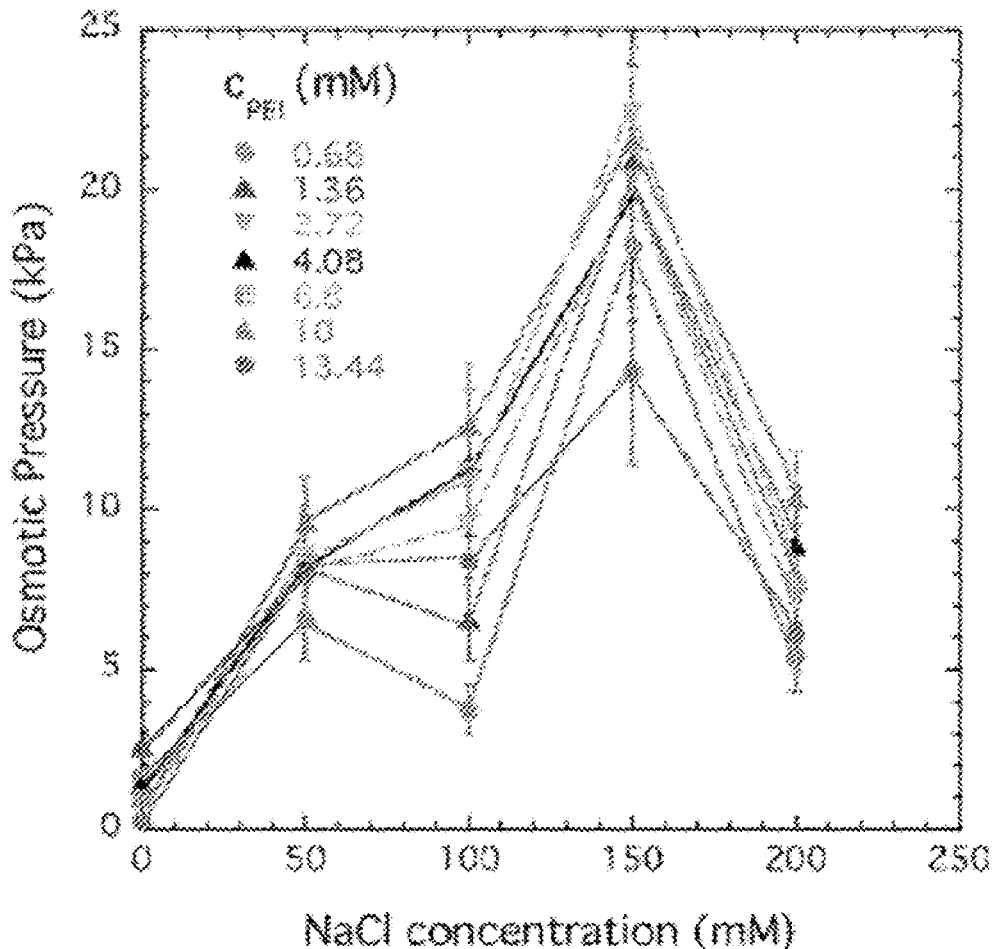
FIG. 5b is a graph that shows osmotic pressure of PEI solutions as a function of NaCl concentration.

The osmotic pressure of the PEI solutions was measured by a Knauer K-7000 Vapor Pressure Osmometer. The osmometer contains two thermistors: a drop of solution was placed on one of the thermistors and a drop of solvent on the other thermistor. Solvent vapor is condensed into the solution because the vapor pressure of the solvent in the solution is smaller than in the pure solvent. The condensation released heat and resulted in a temperature difference between the two thermistors. This temperature difference was detected by measuring the microvolts imbalance on a Wheatstone bridge circuit. In solutions of non-associating solutes the temperature difference is proportional to the number of dissolved particles. In associating solutions, however, the osmotic pressure exhibits either a plateau or a maximum as a function of the polymer concentration. FIG. 5a shows the variation of the osmotic pressure as a function of the PEI concentration for solutions with constant NaCl concentrations. The shape of all curves is qualitatively similar. At low PEI concentration the osmotic pressure increases with the polymer concentration and approaches a plateau at around 2 mM to 4 mM PEI concentration. The observed behavior is typical of associating solutions in which the polymer molecules aggregate due to polar or ionic interactions or hydrogen bonding. In such solutions free polymer chains coexist with large clusters. The results shown in FIG. 5b suggest that a small quantity of NaCl prevents PEI aggregation and increases solubility. The solubility of the 2.5 kDa PEI reaches a maximum at 150 mM NaCl concentration. The decrease of the osmotic pressure at higher salt concentration (>150 mM) can be attributed to screening of the electrostatic repulsion by the added salt.

Figure 6A:
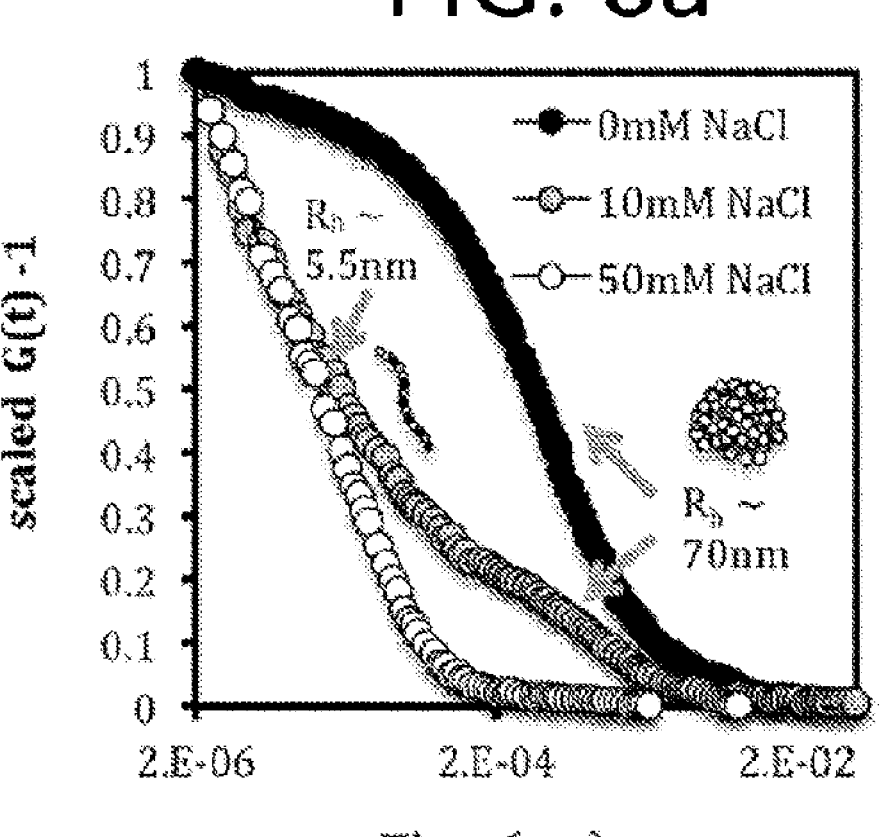
FIGS. 6a-d are graphs showing the distribution of aggregated and free polymer species of PEI based on NaCl concentration.
Figure 6B:
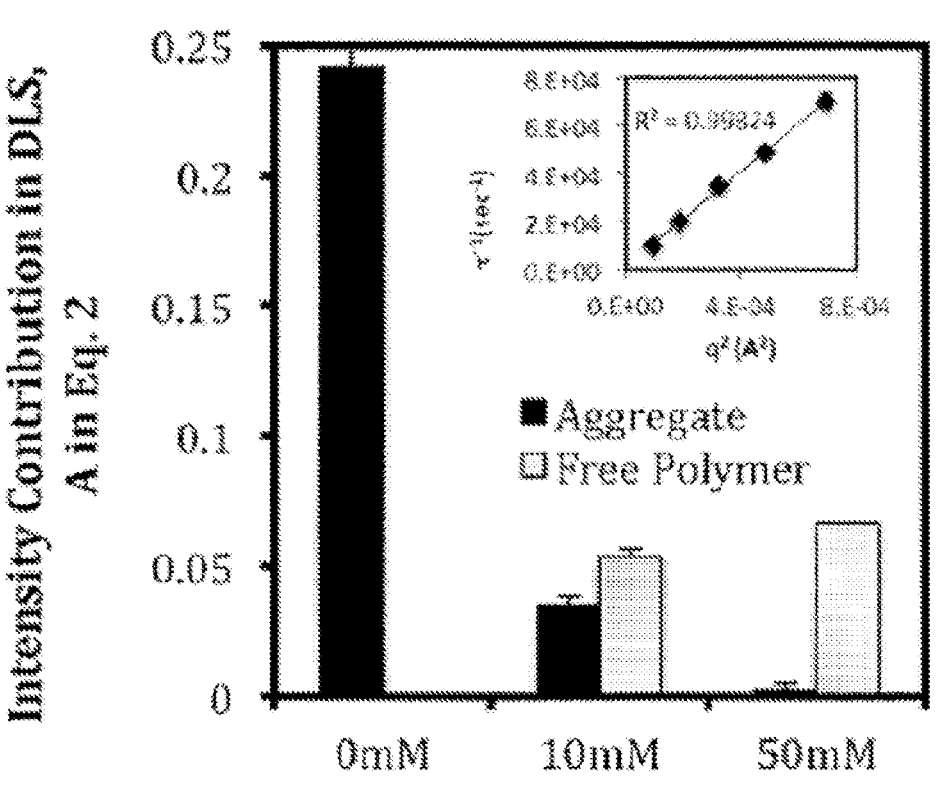
Figure 6C:
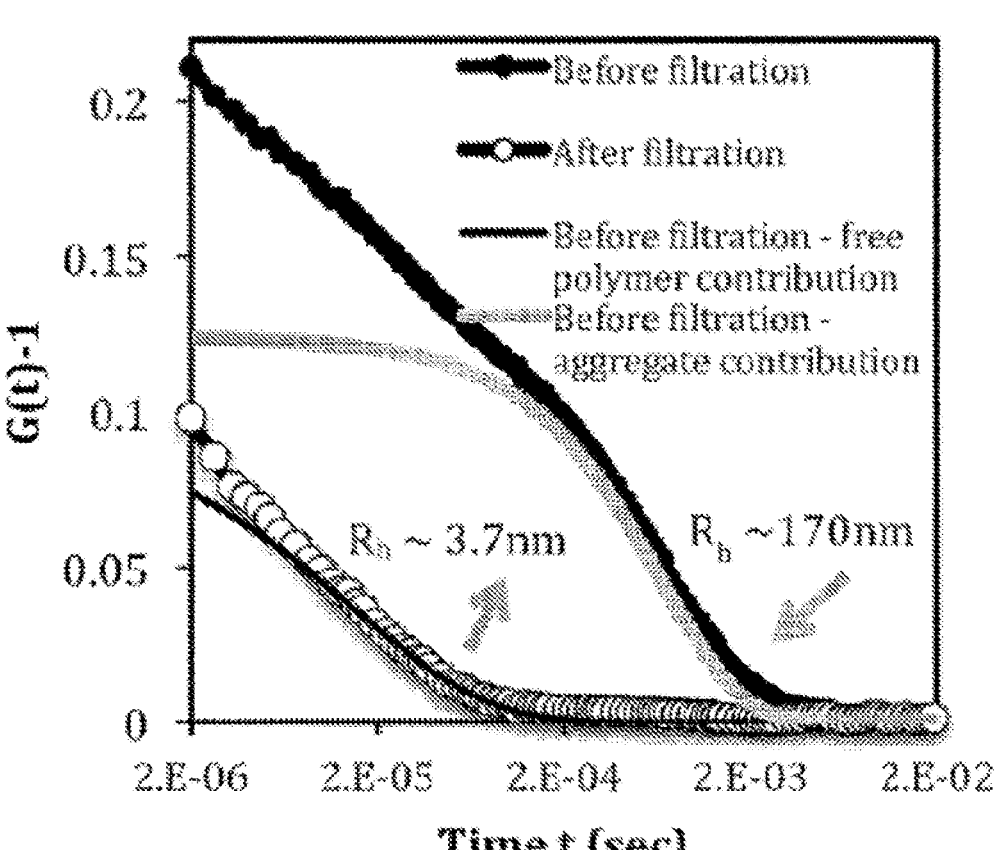
Figure 6D:
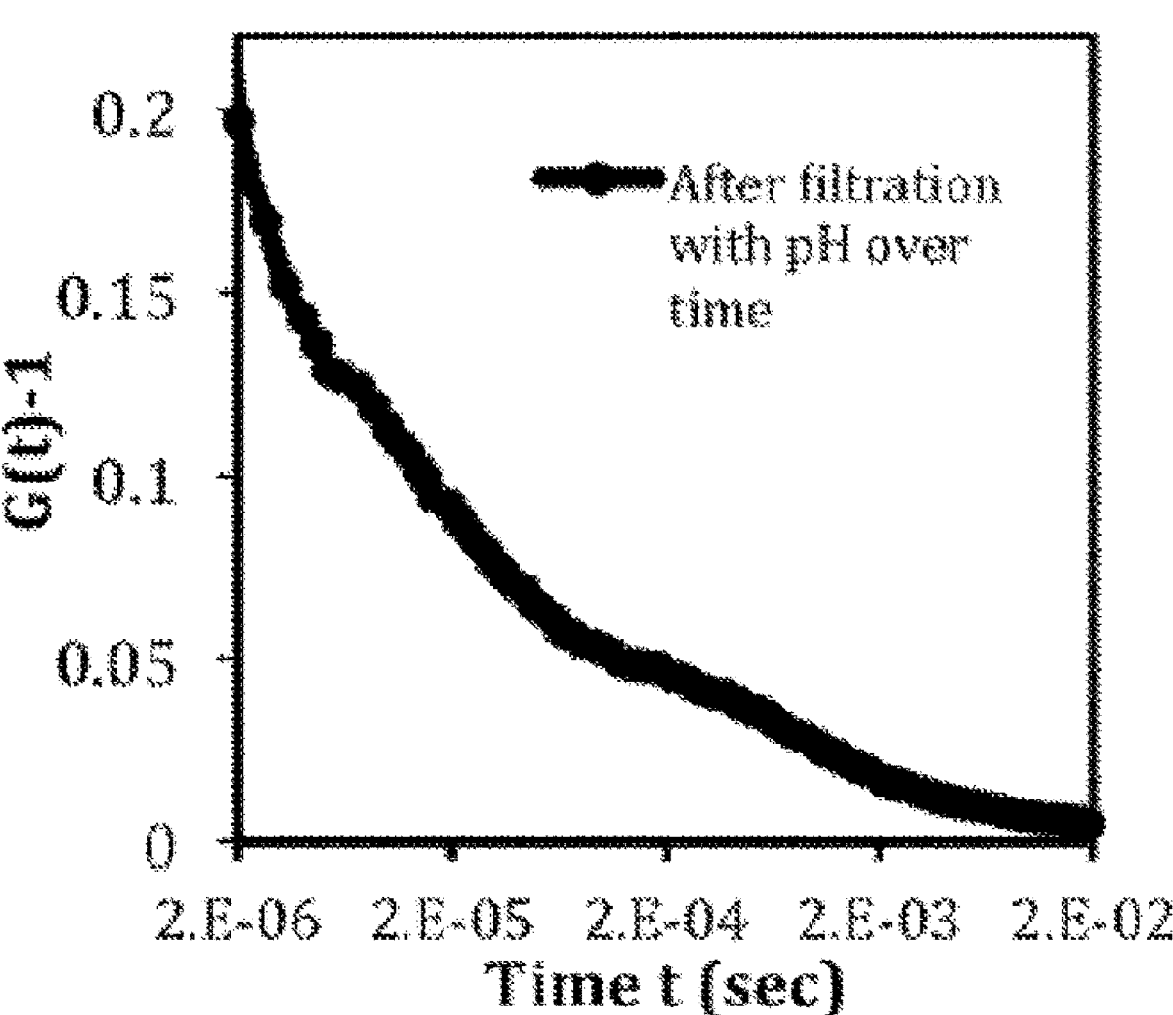

Dynamic light scattering (DLS) of samples was also measured to determine the size of PEI aggregates. DLS measurements of 1 ml PEI solutions in quartz cuvettes (Malvern Instruments, Inc., Westborough, MA) were performed in a Zetasizer ZSP (Malvern Instruments, Inc., Westborough, MA) at 633 nm wavelength and 173° scattering angle. Measurements with multiple scattering angles were performed with a Precision Detector—Expert Laser Light Scattering DLS Workstation equipped with a HeNe laser (wavelength: 698 nm). All samples were then equilibrated at 25° C. for 30 minutes in the light scattering apparatus before measurements. The duration of data collection was 2500 sec because of the relatively low polymer concentration of the PEI solutions. Laser attenuation, sampling position, and sampling time were maintained constant for all measurements. DLS measurements were on a 2.72 mM PEI solution (FIG. 6a). In the absence of added NaCl, the solution showed only one relaxation time corresponding to Rh ~140 nm. This size is much larger than expected for a 2.5 kDa PEI polymer (contour length ~19 nm), indicating that the diffusing entities are large aggregates of many PEI chains. When 10 mM NaCl was added, a faster relaxation mode appeared with Rh ~5 nm, which is within the expected range for free 2.5 kDa polymer. The addition of salt seems to release free polymer from the aggregates. By 50 mM NaCl concentration only one relaxation time due to the free polymer is observed. FIG. 6b demonstrates interconversion between aggregate and free polymer molecules, suggesting that the former is not in a collapsed state but coexists with the free polymer. Filtering PEI solution containing both free and aggregate forms demonstrates that the aggregate is a removable species (FIG. 6c). Filtration through a 200 nm pore size filter removed the species with do of about 340 nm and greater. The disappearance of this slow relaxation component indicates that the aggregates are nearly completely separable by filtration. Only the fast contribution from the free polymer remained after filtration, with the relaxation rate and intensity contribution similar to that before filtration (FIG. 6c). Over time, the aggregates reappeared when the pH of the solution was increased (FIG. 6D). The latter observation indicates that PEI aggregates are not only uncollapsed and removable entities, but are also in dynamic equilibrium with the free polymer.

The osmotic pressure data indicates that the number of free (mobile) entities increases with the addition of salt from zero to 50 mM. Correspondingly in the DLS data, the contribution from free polymers increases as salt concentration increases to 50 mM. Together the two measurements demonstrate the release of free polymers from aggregates as the salt concentration increases.

Zeta Potential of the PEI solutions with only aggregates present were determined with the Malvern Zetasizer ZSP using 1 ml disposable cuvettes, and measurement parameters of 300 sec runtime and 6 runs per sample.

Protonation fraction was also calculated. Fixed volumes of HCl/NaOH with logarithmically increasing molarity were added to separate samples of PEI and NaCl solutions so that the final PEI/NaCl concentration was kept constant. The pH measurements were undertaken after at least 2 hours equilibration using a ThermoScientific Orion pH meter fitted with a Ross Micro probe. There are two important differences between our pH titration method and that typically made in polyelectrolyte solutions. Common methods for polyelectrolyte titrations in which the polymer is first completely charged with the addition of a base/acid and then the completely charged polymers are titrated were not followed because charging the PEI polymer with HCl would also increase its counter-ion content, and would render the solutions not optimal for low salt concentration experiments. Also, typical titrations involving adding acid or base of fixed molarity were avoided because this would dilute the PEI and salt concentration during the titration. In order to maintain the PEI and NaCl concentrations constant, titration was performed by adding fixed volumes of HCl/NaOH of logarithmically increasing molarity to separate samples of PEI solutions. In order to correct for the $H^+$ ions coming from $CO2$ present in distilled water, the overhead space of the PEI solutions was minimized and filled with Nitrogen. Also, controls without PEI were made for each titration sample to keep track of the $H^+$ concentration in the absence of PEI buffering.

PEI in salt-free powder form was used. In this state the PEI polymer is unprotonated, and therefore hydrophobic and undissolvable in plain water. HCl is typically added to dissolve the polymer. From the difference in the amount of HCl added and the amount of H+ remaining in solution (i.e., the pH), it was estimated that the PEI solution needed to be about 33% charged for dissolution to occur. At the physiological pH of about 7.5, the polymer is about 44% charged and dissolved. The salt effect on protonation was studied at pH 7.5. As NaCl was added to the PEI solution, the pH did not change significantly, even though the distribution between free and aggregated polymers changed. In other words, significant amounts of $H^+$ ions (on the order of the amine concentration) were neither taken up nor released as aggregates were converted to free chains. Therefore, it appears that both the PEI aggregates and free polymer forms of PEI have the same charge ratio at neutral pH.

FIG. 7a shows the hydrodynamic radius (Rh) of the free polymer as a function of the concentration of the added salt. The Rh does not decrease monotonically with salt as is typically observed in polyelectrolyte solutions. Instead, Rh initially increases and then decreases. The pH remains within the range of about 7 to 8, indicating that there is less than a 1% change in the apparent PEI protonation for the different salt and polymer concentrations. A possible reason for the initial increase and then decrease of Rh can be attributed to a salt-screening effect (as discussed above with respect to FIG. 5b). The addition of salt initially screens inter-chain repulsions that tend to extend the polymer (left of red curve in FIG. 7*a*) and then proceeds to screen intra-chain repulsions that tend to compact the polymers. FIG. 7*b* shows the distribution of aggregated and free polymers in solutions of FIG. 7*a*, where darker shades denote larger amount of free polymers. For a given PEI concentration, the amount of free polymer increases with the salt content and then decreases again. This trend is consistent with the osmotic data of above (see FIGS. 5*a* and 5*b*) where the number of diffusing entities (i.e. free polymers) initially increases and then decreases with the addition of salt. This change in the free polymer contribution also nearly tracks the inter- and intra-chain repulsion regimes in FIG. 7*a*. The level of aggregation is minimum (i.e. free polymer contribution >95%) in solution conditions where intra-chain repulsion is highest. The osmotic and DLS results both show the biphasic dependence of the aggregation levels on the PEI concentration (FIG. 7*c*).

Figure 8:
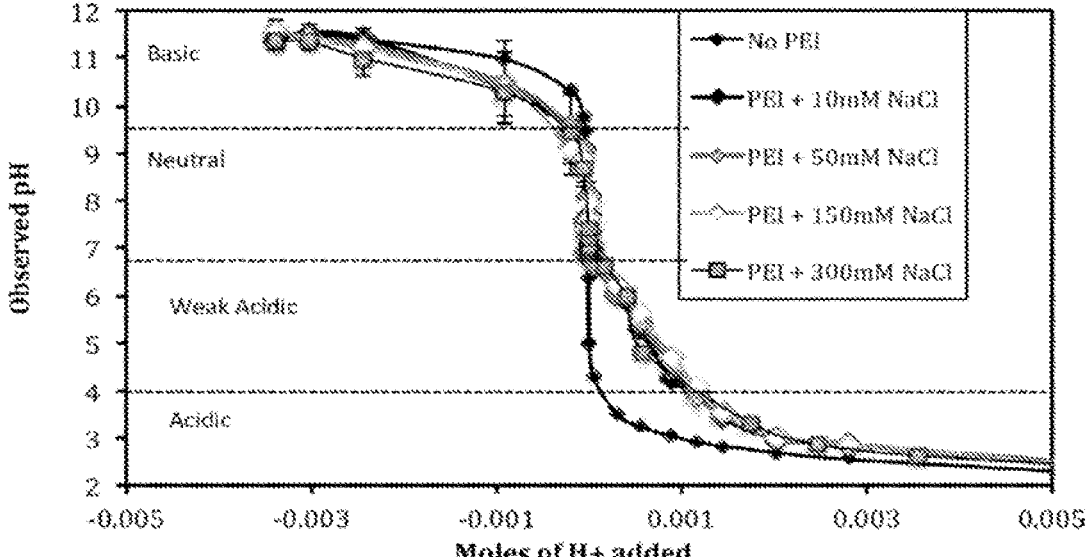
FIG. 8 is a graph of pH titration curves for PEI at different salt concentrations.

FIG. 8 shows the pH titration curve of 4.08 mM PEI for a range of salt concentrations (10*z* 50, 150, 300 mM NaCl). Each $H^+/OH^-$ addition was performed on separate samples in order to maintain both PEI and NaCl concentrations constant. The $H^+$ concentration in the x-axis does not include the $H^+$ ions added during dissolution of the stock solution. The polyelectrolyte state of 4.08 mM PEI at neutral pH changes as the salt concentration increases from 10 to 300 mM NaCl. The aggregation level varies from about 20% to about 5% and then goes back to about 20% (see FIG. 7*b*). However, there is no significant difference in the shape of the titration curves. The relative salt-independence of the titration profile indicates that the protonation or charge ratio of PEI (given by the titration profile) is unaffected by the levels of aggregation and the intra- vs. inter-chain charge repulsion (determined by the salt concentration). The linear PEI titration curves in FIG. 8 show two pKa. The pKa of about 4.5 can be attributed to the protonation of the free polymers which are the abundant species in acidic regime. The pKa of about 10 can be attributed to the protonation of the aggregates which are the abundant species in basic regime.

Figures 9A, 9B, 9C:
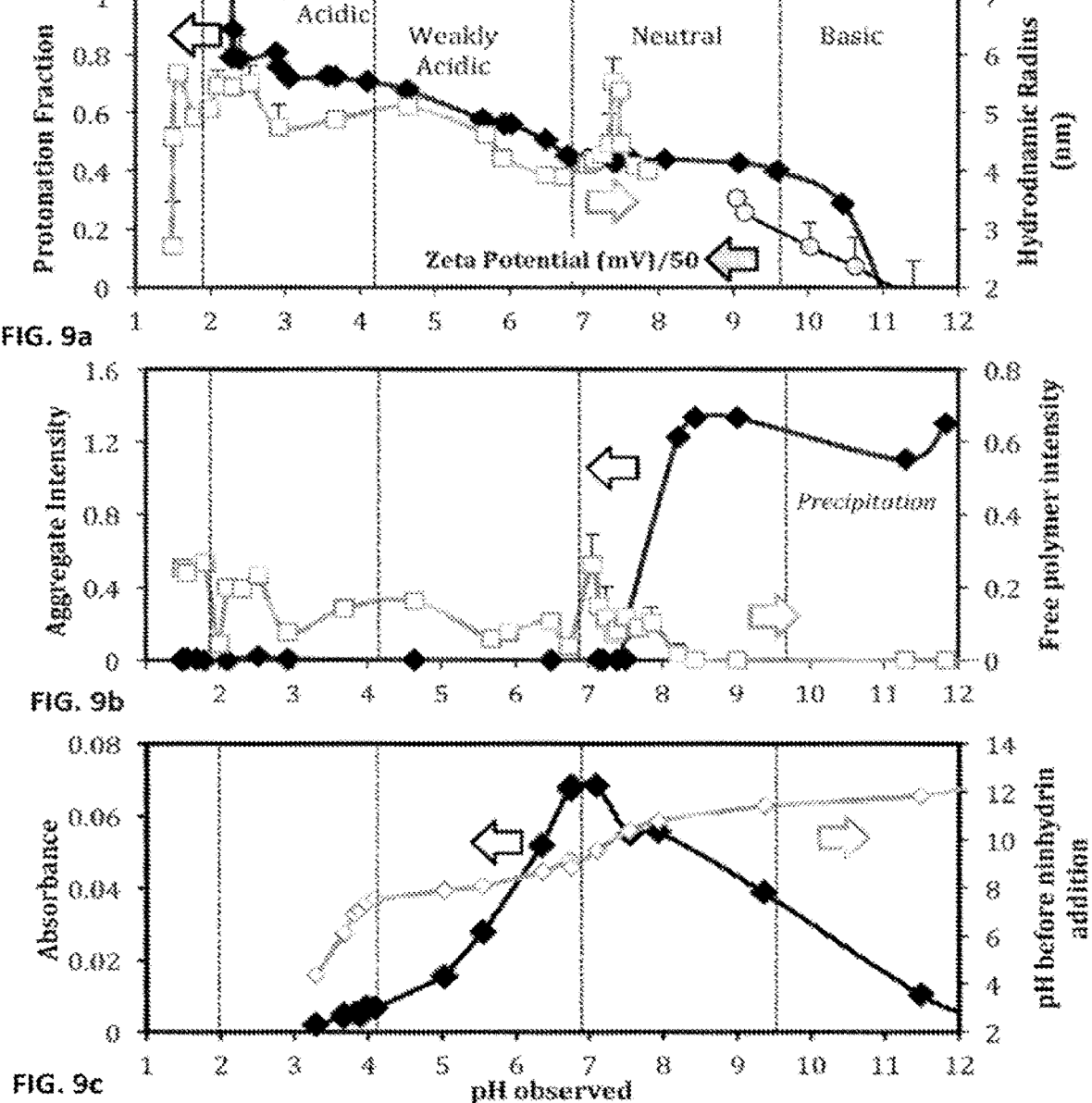
FIGS. 9a to 9c are graphs demonstrating protonation-polyelectrolyte interplay of PEI in solution with 150 mM NaCl as a function of pH.

Changes in protonation and polyelectrolyte state during the pH titration of the 4.08 mM PEI solution was observed, as shown in FIG. 9, for the 150 mM NaCl sample where the polymer has high intra-chain repulsion and is present mostly in the free polymer state at neutral pH. The $H^+$ uptake, shown in FIG. 9*a*, was monitored by calculating the protonation ratio for each sample. The polyelectrolyte state was tracked by following the intensity contribution from the free and aggregated PEI forms and hydrodynamic diameter of the free polymer. To enable meaningful comparison of intensity contributions, the DLS laser attenuation and sampling position were maintained constant for all samples. The results are discussed in terms of four pH region. In the basic region (pH of about 9.5 to about 12), the aggregate is the dominant form and its charge falls from ~44% to negative values (FIG. 9*a*). The decrease in the aggregate's positive charge is also reflected by the zeta potential which falls from 7±4 mV at pH=10 to near 0 mV at pH=11, where the polymer precipitates. In the neutral region (pH of about 6.8 to about 9.5), the net PEI protonation remains constant at 44%. The aggregate is the only form present at a pH of 9.5, and it gradually converts to free chains as the pH reduces from 9.5 to about 7 (FIG. 9*b*). The extent of aggregate to free chain conversion depends on the salt concentration, and the zeta potential of the aggregate at a pH of 9 is about 15.3±1.1 mV. Free polymer chains become detectable below a pH of 8, and their hydrodynamic radii exhibit a maximum at around pH 7.5. In the weak acidic region (pH of about 4 to about 6.8), the free PEI chains dominate the scattering response (FIG. 9*b*). Buffering is observed as the polymer protonation increases steadily from about 44% to about 70% (FIG. 9*a*). The hydrodynamic diameter of the free polymer increases with protonation, which is expected due to the intra-chain repulsion in the increasingly charged polymer. In the acidic region (pH of about 2 to about 4), the buffering capacity decreases while PEI protonation remains nearly constant at 66 to 70% (FIG. 9*a*). The hydrodynamic radius decreases, suggesting that the free polymer chains are gradually compacted possibly due to interchain repulsion between the highly charged polyions. Below a pH of about 3 the protonation rapidly increases and reaches about 95% (FIG. 9*b*). Correspondingly, Rh exhibits a peak value and remains constant. Beyond a pH of 2, there is no significant buffering since the polymer has reached its maximum protonation.

Ninhydrin assay was used to verify the pH dependence of PEI's protonation. The assay was performed on 4.08 mM PEI solutions in 150 mM NaCl at various pH. Secondary amines react with ninhydrin in acidic medium to give iminium salt. The iminium salt has a characteristic yellow color with optimum UV-Vis absorbance at 440 nm. During the assay a fixed amount of acid was added to all PEI solutions. The pH of the PEI solutions before and after acid addition are shown in FIG. 9*c* (plot with unfilled diamonds). The slope of the plot reflects the buffering capacity of the polymer. For instance, the slope is lower in the 'weak acidic' and 'basic' regions where the buffering capacity is high, and the slope is high in the 'neutral' and 'acidic' regions where the buffering capacity is low. In the 'weak acidic' and 'basic' regions, the free polymer buffers the removal of H+ ions by changing its protonation; therefore, the solution pH changes slowly. In the 'neutral' and 'acidic' regions the polymer protonation state does not vary notably, and therefore the slope is greater. The formation of the iminium salt requires both a transferable electron pair on the amine nitrogen and an acidic medium. The reaction between ninhydrin and a secondary amine to form the iminium salt proceeds in two stages: (1) the lone-pair of electrons from the nitrogen of PEI's secondary amine is transferred to the ninhydrin complex; and (2) the ninhydrin complex undergoes hydrolysis in the acidic medium to form iminum salt Acidic pH decreases iminium salt formation in linear PEI (i.e., absorbance decreases in the 'weak acidic' region, FIG. 9*c*), which can be attributed to the decrease in the number of nitrogen atoms being able to donate lone-pair of electrons as they become protonated. In other words the absorbance, and therefore the iminium salt formation, should track the PEI protonation profile as demonstrated in FIG. 9*c*. The absorbance changes slowly around a pH of about 7 where the protonation stalls at 44%, falls rapidly from a pH of 7 to a pH of 4 (in the 'weakly acidic' region) where the polymer protonation increases, and changes slowly from a pH of 4 to a pH of 3, where the polymer protonation stalls again, and becomes negligible beyond a pH of 3 where the polymer protonation is near complete.

The results indicate that PEI exists in two forms and the size of the free polymer chain depends on the salt concentration and the nature of charge repulsion. The level of protonation of the polymer can be controlled by the pH of the solution. In the context of DNA delivery application it is essential to know how the protonation/polyelectrolyte state of PEI affects its interaction with DNA and the subsequent formation of DNA-PEI nanoparticles. The PEI polymer shows large changes in charge, size, and aggregation within the same salt and pH range. Therefore the size of the DNA-PEI complexes to were tracked to examine if they correlated with the protonation/aggregation state of PEI.

Figure 10:
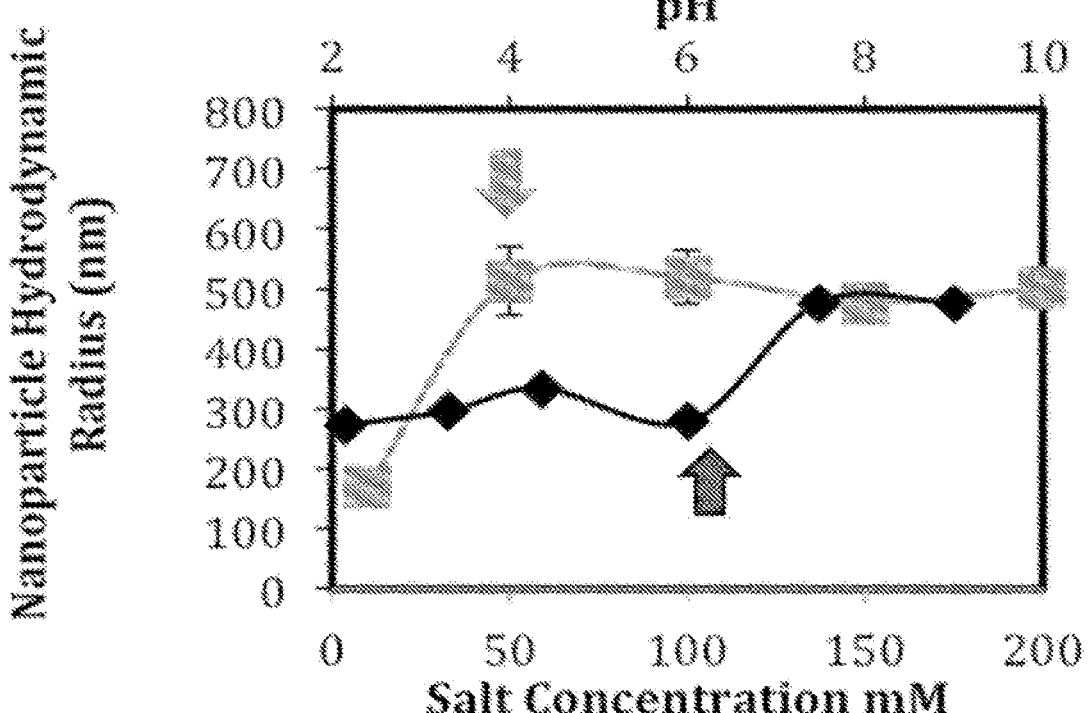
FIG. 10 is a graph illustrating the size of PEI nanogels as a function of salt concentration.

Such correlation would indicate an obvious dependence between the PEI state and the DNA-PEI interactions leading to nanoparticle packing. FIG. 10 shows the hydrodynamic radii of nanoparticles packed in 4.08 mM PEI solutions at different NaCl concentrations but at constant pH (about 7.5). Despite the differences in the PEI polyelectrolyte states, the size of the nanoparticles is similar, except for the sample with 10 mM salt concentration. The smaller nanoparticle size in 10 mM NaCl reflects stronger charge-repulsion at low salt-screening conditions that prevents the aggregation of nanoparticles. Overall, results indicate that in near physiological salt conditions the aggregation state of PEI does not significantly influence the nanoparticle radii.

FIG. 10 also shows the hydrodynamic radii of nanoparticles packed in 4.08 mM PEI solutions at different pH at constant (150 mM) salt concentration. The change of nanoparticle size with pH indicates that polymer charge affects DNA packing. There was no significant change in nanoparticle size between a pH of 7.5 and a pH of 9. At these two pH values, the PEI polymers have the same charge, but different aggregation levels. The constancy of the nanoparticle size appears to again demonstrate that DNA-PEI interactions are practically independent of the PEI's aggregation state.

Example 2

Macromolecules and charged oligosaccharides are added to a solution containing linear PEI. The charged oligosaccharides and macromolecules bind to the charged, hydrophobic PEI polymers. The polymer is crosslinked with an am inecrosslinking agent to form PEI carrier structures and contain the charged molecules associated within the aggregated polymer structure. Sodium chloride salt is then added to the solution to raise chloride ion concentration to greater than 200 mM and induce collapse of the PEI carrier structures. The carrier structures are isolated and added to a formulation provided to a patient for oral ingestion.

During transit of the ingested formulation through the digestive tract, the carrier structures are in a collapsed state during passage through the stomach, where the high chloride ion concentration and pH of about 3 promote PEI aggregation. This protects the oligosaccharides and macromolecules in a shell formed from relatively impermeable PEI gel.

Upon entering the small intestine, the PEI gel carrier structures begin to swell as chloride ion concentration decreases and pH increases. The transported macromolecules and free oligosaccharides are released. The oligosaccharides make the mucous less viscous so that therapeutic macromolecules are allowed to diffuse to the epithelial surface.

As the carrier structures pass through the rectum, the even lower environmental concentration of chloride ions results in collapse of the structure, reducing the likelihood of the PEI carriers dissociating and allowing the carrier structures to be more efficiently excreted.

Example 3

PEI carriers are used as nano-archiving components for blood or other fluids. A sample of fluid is obtained containing fluids having different surface interactions. Nanoparticles are added to sequester cationic and hydrophobic macromolecules. PEI is then added, which binds anionic macromolecules within the fluid. Some PEI chains may be tagged with a marker. Sodium chloride is added to the solution to cause aggregation and compaction of PEI around anionic macromolecules. A crosslinking agent is added to the solution to bind the aggregated PEI chains.

Crosslinked PEI samples may be stored in a container, and macromolecules may be released by adding water to dilute sodium chloride concentration. Different samples, for instance fluid samples obtained at different points in time, may be stored in a single container with different markers associated with each sample. The PEI carriers may then be separated by marker, for instance using microflow cytometry to separate carriers by their associated markers. Once separated, release of macromolecule samples can be effected by reducing sodium chloride concentration, and swollen carriers can be again compacted for storage by the addition of sodium chloride.

Example 4

PEI carriers may be utilized as reversible "shrinkwrapping" for portability and biological interfacing of diagnostic and/or therapeutic platforms. Nanochips, nanosensors, sensing macromolecules, and/or other materials may be stored in PEI carriers forming nanocompartments by the addition of linear PEI and crosslinking agent, and increasing anion concentration to induce compaction. A plurality of nanocompartments may be packed into macroscale packages. Adding a dilute solution to lower anion concentration promotes swelling of the PEI nanocompartments, allowing small molecules to diffuse into the nanocompartments and interact with the sensors located therein. After sensing is complete, the macroscale package may be washed in tap water, removing the detected small molecules and compacting the nanocompartments for later use.

Alternatively, nanocompartments containing nanochips, nanosensors, sensing macromolecules, and/or other materials may be deposited in nanocarriers for drug delivery and gene therapy. The nanocarriers are broken down as they reach target cells or tissues, and physiological salt conditions cause swelling of the PEI nanocompartments, resulting in a semi-permeable barrier that allows only small molecules to diffuse into the nanocompartment and interact with sensors in the crowded tissue or cell environment.

What is claimed:

1. A method of delivering a substance to a mammal, the method comprising:
    subjecting a composition comprising a nanogel particle comprising crosslinked linear polyethyleneimine and the substance to a sodium chloride concentration of less than about 50 mM or greater than about 200 mM to compact the nanogel particle; and
    providing the nanogel particle to the mammal for oral delivery.

2. The method of claim 1, further comprising combining the particle with an excipient prior to the step of providing the particle to the mammal.

3. The method of claim 1, wherein the substance is a therapeutic macromolecule.

4. The method of claim 1, wherein the nanogel particle is transitionable between a swollen semipermeable state and a relatively impermeable compact state in response to surrounding anion concentrations, and
    wherein the anion concentrations is 10 mM to 200 mM.

5. The method of claim 1, wherein the linear polyethyleneimine is crosslinked by an amine crosslinking agent.

6. The method of claim 5, wherein the amine crosslinking agent comprises at least two aldehyde groups.

7. The method of claim 6, wherein the amine crosslinking agent is glutaraldehyde.

8. The method of claim 1, wherein the linear polyethyleneimine chains have a mass of about 2.5 to about 25 kDA.

9. The method of claim 3, further comprising at least one nanochip, nanosensor, or sensing macromolecule.

10. The method of claim 1, wherein the linear polyethyleneimine is crosslinked by a crosslinking agent having at least two aldehyde groups and surrounds at least one therapeutic macromolecule, nanochip, nanosensor, or sensing-macromolecule in the compact state.

11. The method of claim 1, wherein the nanoparticle particle has a maximum dimension of about 50 to about 500 nm.

* * * * *